(12) United States Patent
Heger et al.

(10) Patent No.: US 12,349,950 B2
(45) Date of Patent: Jul. 8, 2025

(54) CERCLAGE SYSTEM AND METHODS OF USE THEREOF

(71) Applicant: DEPUY SYNTHES PRODUCTS, INC., Raynham, MA (US)

(72) Inventors: Veronika Heger, Eagleville, PA (US); Binh Vu, Thorndale, PA (US); Peter Fatone, Exton, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 364 days.

(21) Appl. No.: 17/949,767

(22) Filed: Sep. 21, 2022

(65) Prior Publication Data

US 2023/0263559 A1     Aug. 24, 2023

Related U.S. Application Data

(60) Provisional application No. 63/312,575, filed on Feb. 22, 2022.

(51) Int. Cl.
*A61B 17/82*     (2006.01)

(52) U.S. Cl.
CPC ................... *A61B 17/82* (2013.01)

(58) Field of Classification Search
CPC ....................................................... A61B 17/82
See application file for complete search history.

(56) References Cited

U.S. PATENT DOCUMENTS

| | | | |
|---|---|---|---|
| 5,766,218 A | 6/1998 | Arnott | |
| 5,797,915 A | 8/1998 | Pierson, III et al. | |
| 8,162,942 B2 | 4/2012 | Coati et al. | |
| 8,613,755 B1 | 12/2013 | Foerster | |
| 9,131,968 B2 | 9/2015 | Cavallazzi et al. | |
| 2013/0245699 A1 | 9/2013 | Orbay et al. | |
| 2021/0378724 A1* | 12/2021 | Kobayashi | A61B 17/82 |

FOREIGN PATENT DOCUMENTS

WO     2015026359 A1     2/2015

OTHER PUBLICATIONS

Increased Fracture Site Compression Using Shape Memory Alloy for Cerclage Wire Fixation, Sears et al., 47th Annual Meeting, Orthopaedic Research Society, San Francisco, California, Feb. 25-28, 2001.
Cable System Surgical Technique For Orthopaedic Trauma Surgery, DePuy Synthes, Synthes GmbH, Eimattstrasse 3, 4436 Oberdorf, Switzerland, 2017.

* cited by examiner

*Primary Examiner* — Olivia C Chang
(74) *Attorney, Agent, or Firm* — Christopher L. Makay

(57) ABSTRACT

A cerclage system used to affix a bone includes a tension plate, a cable lock, and a cerclage cable configured to encircle the bone. The tension plate, which is engageable with the cerclage cable, is moveable between a natural shape and an insertion shape where the tension plate stores energy. The cable lock locks the cerclage cable about the bone in engagement with the tension plate. The tension plate is configured for positioning atop the bone while residing in the insertion shape. The tension plate, through an engagement thereof with the cerclage cable and upon attempted movement thereof from the insertion shape toward the natural shape, delivers the energy stored therein to the cerclage cable thereby tensioning the cerclage cable such that the cerclage system continuously compresses the bone.

18 Claims, 16 Drawing Sheets

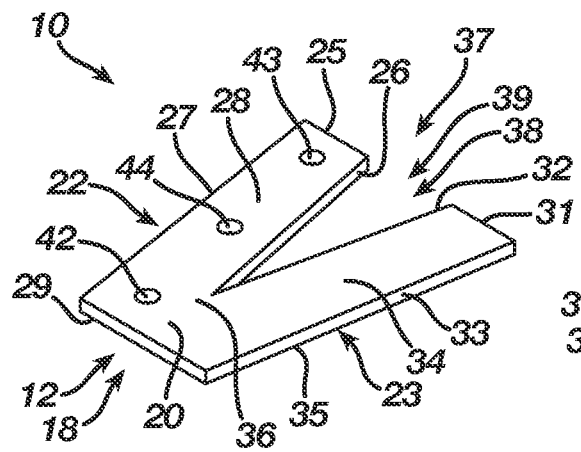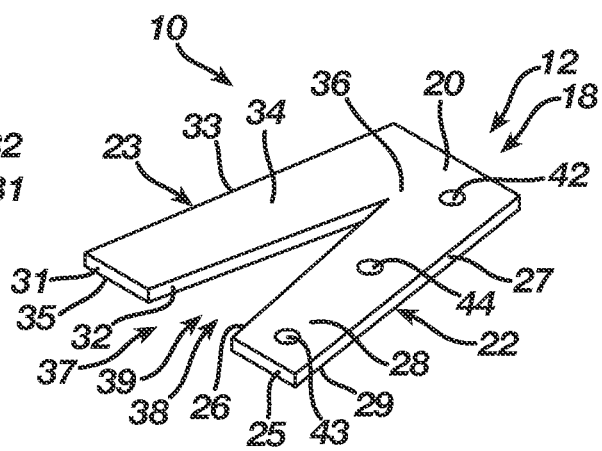
FIG. 3A  FIG. 3B
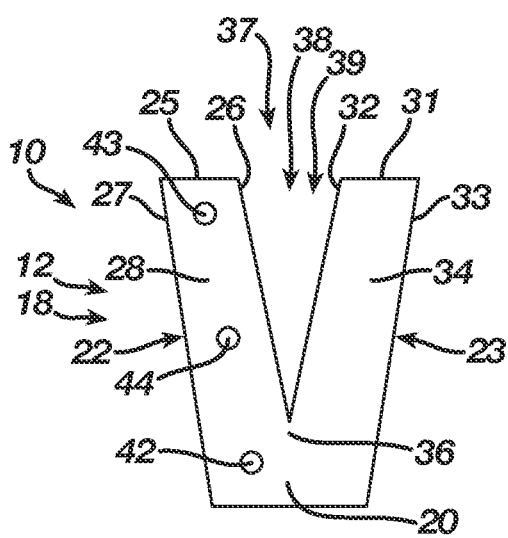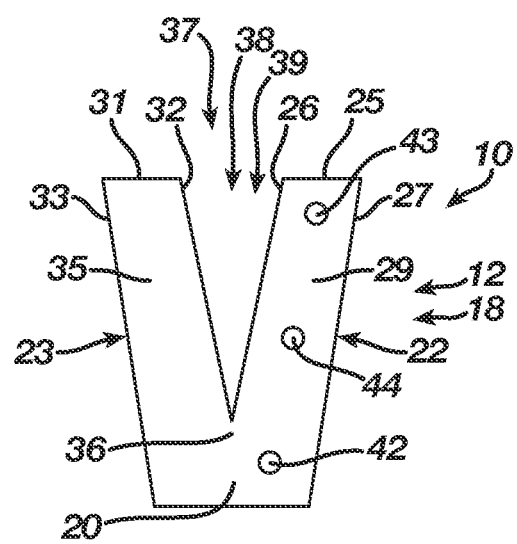
FIG. 3C  FIG. 3D

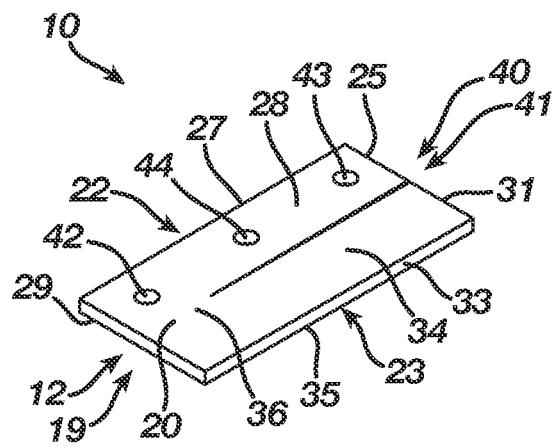 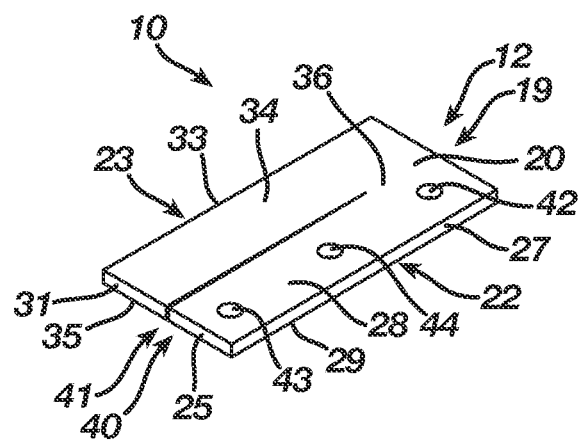
FIG. 4A  FIG. 4B
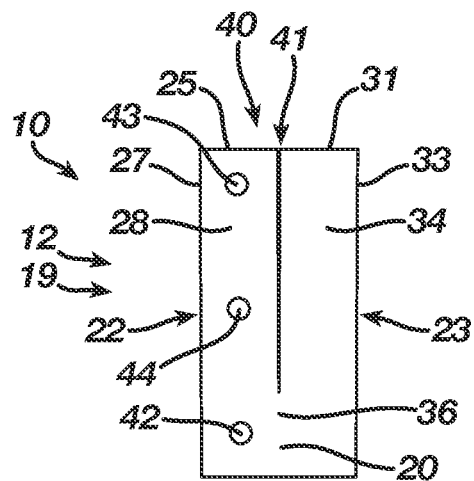 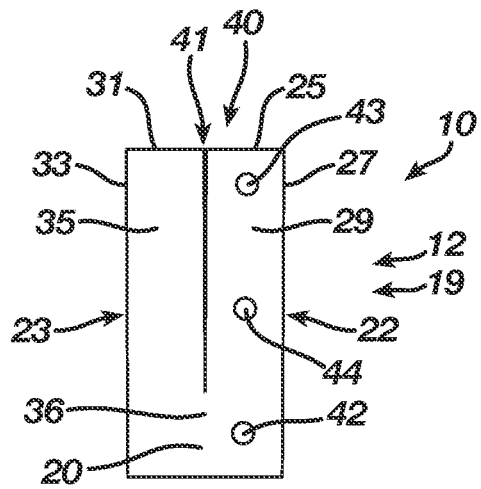
FIG. 4C  FIG. 4D

CERCLAGE SYSTEM AND METHODS OF USE THEREOF

BACKGROUND OF THE INVENTION

1. Field of the Invention

The present invention relates to fixation of bone, bones, or bone pieces in a desired alignment that promotes a healing thereof and, more particularly, but not by way of limitation, to a cerclage system for affixing bone, bones, or bone pieces.

2. Description of the Related Art

Fixation of bone, bones, or bone pieces in a desired alignment during an orthopedic surgery in order to promote a healing thereof often involves use of screws inserted into the bone, bones, or bone pieces and/or one or more bone plates secured with the bone, bones, or bone pieces via screws. Although screws and/or bone plates operate adequately in bone fixation, there are instances where it is not possible to insert screws into the bone, bones, or bone pieces. As an illustration, certain bones or bone pieces are too small for a corrective fixation using a screw received therein, or, in a periprosthetic case, an existing implant may prevent screw insertion.

In order to overcome an inability to insert screws, cerclage wires have been developed. A cerclage wire encircles a bone, bones, or bone pieces and holds the bone, bones, or bone pieces in a desired alignment that promotes a healing thereof. The cerclage wire, which inserts through a wire lock, is tensioned, and then, after crimping of the wire lock, the cerclage wire maintains the bone, bones, or bone pieces in a desired alignment. The cerclage wire may be used with one or more Kirschner wires inserted into the bone, bones, or bone pieces that assist in securing the cerclage wire with the bone, bones, or bone pieces. Furthermore, the cerclage wire when encircling the bone, bones, or bone pieces may engage and thus secure a bone plate atop the bone, bones, or bone pieces such that the bone plate holds the bone, bones, or bone pieces in the desired alignment.

While cerclage wires operate adequately in holding bone, bones, or bone pieces in a desired alignment that promotes a healing thereof, cerclage wires do experience certain disadvantages. Illustratively, cerclage wires encircling a bone, bones, or bone pieces do not provide continuous compression. Moreover, cerclage wires over time are prone to lose tension, potentially permitting a movement of the bone, bones, or bone pieces and a resulting misalignment that produces less than adequate healing thereof.

Accordingly, a cerclage system that fixates bone, bones, or bone pieces in a desired alignment that promotes a healing thereof while imparting continuous compression to the bone, bones, or bone pieces will provide improvements in cerclage systems.

SUMMARY OF THE INVENTION

In accordance with the present invention, a cerclage system is used to affix bone, bones, or bone pieces. The cerclage system includes a tension plate, a cable lock, and a cerclage cable with a length sufficient to encircle the bone, bones, or bone pieces. The tension plate, which is engageable with the cerclage cable, is moveable between a natural shape and an insertion shape whereby the tension plate stores energy. The cable lock locks the cerclage cable about the bone, bones, or bone pieces in engagement with the tension plate. The tension plate is configured for positioning atop the bone, bones, or bone pieces while residing in the insertion shape. The tension plate, through an engagement thereof with the cerclage cable and upon attempted movement thereof from the insertion shape toward the natural shape, delivers the energy stored therein to the cerclage cable thereby tensioning the cerclage cable such that the cerclage system continuously compresses the bone, bones, or bone pieces.

The cerclage system may include a positioning pin and a bone plate. The positioning pin is engageable with the cerclage cable and further with the tension plate in order to secure the positioning pin with the tension plate. The bone plate is engageable with the cerclage cable and further with the bone, bones, or bone pieces. The bone plate, upon the tension plate tensioning the cerclage cable, assists in continuously compressing the bone, bones, or bone pieces.

The tension plate includes a base, a first arm extending from the base to a distal end, and a second arm extending from the base to a distal end. The base proximate the first arm and the second arm includes a transition section. The tension plate in the natural shape includes the base through the transition section thereof moving the first arm and the second arm to locate the first arm and the second arm in a natural position whereby the first arm and the second arm expand such that the first arm at the distal end thereof and the second arm at the distal end thereof are spaced apart at a first distance. The tension plate in the insertion shape includes the base through the transition section thereof deforming to store energy while moving the first arm and the second arm to locate the first arm and the second arm in an insertion position whereby the first arm and the second arm contract such that the first arm at the distal end thereof and the second arm at the distal end thereof are spaced apart at a second distance that is less than the first distance.

The engagement of the tension plate with the cerclage cable includes the first arm and the second arm engaging the cerclage cable. Upon the tension plate attempting movement from the insertion shape toward the natural shape, the base through the transition section thereof attempts to move the first arm and the second arm from the insertion position to the natural position. As a result, the first arm and the second arm attempt to expand whereby the first arm and the second arm tension the cerclage cable such that the cerclage system continuously compresses the bone, bones, or bone pieces.

The first arm includes at least a first aperture configured to receive a fixation device that secures the tension plate with the bone, bones, or bone pieces. Upon the tension plate attempting movement from the insertion shape toward the natural shape, the base through the transition section thereof attempts to move the first arm and the second arm from the insertion position to the natural position. As a result, the second arm, due to a securing of the first arm with the bone, bones, or bone pieces, attempts to expand from the first arm whereby the second arm tensions the cerclage cable such that the cerclage system continuously compresses the bone, bones, or bone pieces.

The first aperture of the first arm further is configured to receive the positioning pin, whereas the positioning pin is configured to fit within the first aperture thereby securing the positioning pin with the tension plate. The engagement of the tension plate with the cerclage cable includes the first arm engaging the cerclage cable through a coupling of the cerclage cable with the positioning pin fit within the first aperture of the first arm and the second arm engaging the cerclage cable. Upon the tension plate attempting movement from the insertion shape toward the natural shape, the base through the transition section thereof attempts to move the first arm and the second arm from the insertion position to the natural position. As a result, the first arm and the second arm attempt to expand whereby the first arm and the second arm tension the cerclage cable such that the cerclage system continuously compresses the bone, bones, or bone pieces.

The first arm includes at least the first aperture configured to receive a fixation device that secures the tension plate with the bone, bones, or bone pieces and a second aperture. The second aperture is configured to receive the positioning pin, whereas the positioning pin is configured to fit within the second aperture of the first arm thereby securing the positioning pin with the tension plate. The engagement of the tension plate with the cerclage cable includes the first arm engaging the cerclage cable through a coupling of the cerclage cable with the positioning pin fit within the second aperture of the first arm and the second arm engaging the cerclage cable. Upon the tension plate attempting movement from the insertion shape toward the natural shape, the base through the transition section thereof attempts to move the first arm and the second arm from the insertion position to the natural position. As a result, the second arm, due to a securing of the first arm with the bone, bones, or bone pieces, attempts to expand from the first arm whereby the second arm tensions the cerclage cable such that the cerclage system continuously compresses the bone, bones, or bone pieces.

The first arm includes the first aperture and the second aperture configured to receive a fixation device that secures the tension plate with the bone, bones, or bone pieces and a third aperture. The third aperture is configured to receive the positioning pin, whereas the positioning pin is configured to fit within the third aperture of the first arm thereby securing the positioning pin with the tension plate. The first arm includes the first aperture located adjacent the base of the tension plate, the second aperture located adjacent the distal end of the first arm, and the third aperture located between the first aperture and the second aperture. The engagement of the tension plate with the cerclage cable includes the first arm engaging the cerclage cable through a coupling of the cerclage cable with the positioning pin fit within the third aperture of the first arm and the second arm engaging the cerclage cable. Upon the tension plate attempting movement from the insertion shape toward the natural shape, the base through the transition section thereof attempts to move the first arm and the second arm from the insertion position to the natural position. As a result, the second arm, due to a securing of the first arm with the bone, bones, or bone pieces, attempts to expand from the first arm whereby the second arm tensions the cerclage cable such that the cerclage system continuously compresses the bone, bones, or bone pieces.

The cerclage system affixes a bone, bones, or bone pieces in a method as follows. Once the tension plate is constrained in the insertion shape, the bone, bones, or bone pieces are aligned at a fusion zone. The tension plate in the insertion shape is positioned atop the bone, bones, or bone pieces across the fixation zone. The cerclage cable encircles the bone, bones, or bone pieces such that the tension plate engages the cerclage cable. Upon tensioning the cerclage cable about the bone, bones, or bone pieces, the cable lock locks the cerclage cable about the bone, bones, or bone pieces in engagement with the tension plate. After releasing the constraining of the tension plate in the insertion shape, the tension plate, through the engagement thereof with the cerclage cable and upon attempted movement thereof from the insertion shape toward the natural shape, delivers the energy stored therein to the cerclage cable thereby tensioning the cerclage cable such that the cerclage system continuously compresses the bone, bones, or bone pieces.

The positioning of the tension plate in the insertion shape atop the bone, bones, or bone pieces across the fixation zone includes securing the tension plate to the bone, bones, or bone pieces using a fixation device. The engagement of the tension plate with the cerclage cable includes securing a positioning pin with the tension plate and engaging the cerclage cable with the positioning pin. The method for the cerclage system may further include securing a bone plate with the bone, bones, or bone pieces followed by securing the cerclage cable with the bone plate, whereby, upon the tension plate tensioning the cerclage cable, the bone plate assists in continuously compressing the bone, bones, or bone pieces.

It is therefore an object of the present invention to provide a cerclage system that fixates bone, bones, or bone pieces in a desired alignment that promotes a healing thereof.

It is a further object of the present invention to provide a cerclage system that imparts continuous compression to the bone, bones, or bone pieces.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF THE DRAWINGS

FIGS. 3A and 3B are isometric views illustrating an alternative of the tension plate of the cerclage system transitioned to the natural shape.

FIG. 3C is a top view illustrating the alternative tension plate of the cerclage system transitioned to the natural shape.

FIG. 3D is a bottom view illustrating the alternative tension plate of the cerclage system transitioned to the natural shape.

FIGS. 4A and 4B are isometric views illustrating the alternative tension plate of the cerclage system transitioned to the insertion shape.

FIG. 4C is a top view illustrating the alternative tension plate of the cerclage system transitioned to the insertion shape.

FIG. 4D is a bottom view illustrating the alternative tension plate of the cerclage system transitioned to the insertion shape.

DETAILED DESCRIPTION OF THE PREFERRED EMBODIMENTS

Figure 1A:
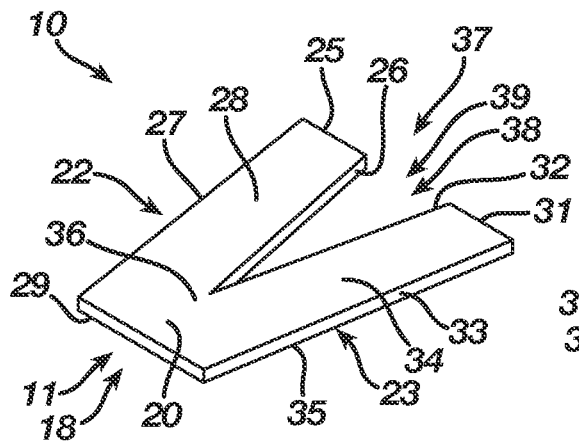
FIGS. 1A and 1B are isometric views illustrating a tension plate of a cerclage system transitioned to a natural shape.
Figure 1B:
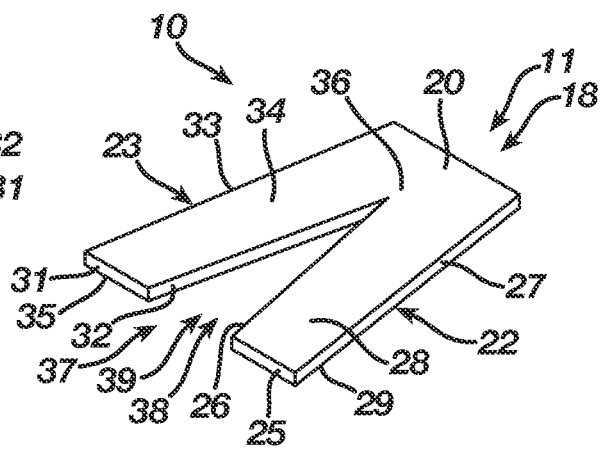
Figure 1C:
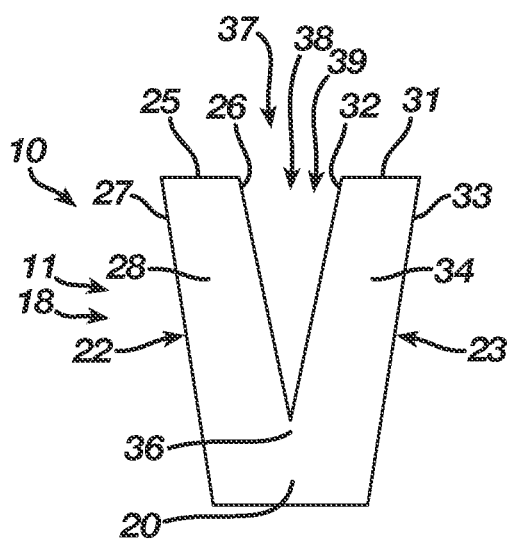
FIG. 1C is a top view illustrating the tension plate of the cerclage system transitioned to the natural shape.
Figure 1D:
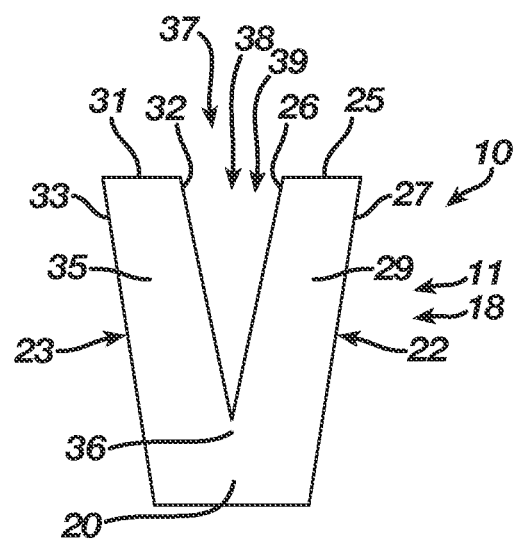
FIG. 1D is a bottom view illustrating the tension plate of the cerclage system transitioned to the natural shape.
Figure 2A:
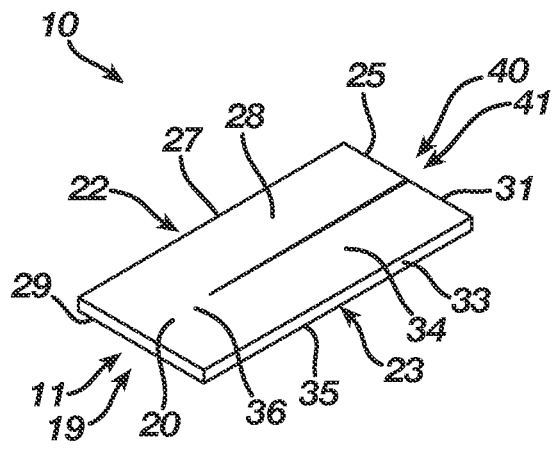
FIGS. 2A and 2B are isometric views illustrating the tension plate of the cerclage system transitioned to an insertion shape.
Figure 2B:
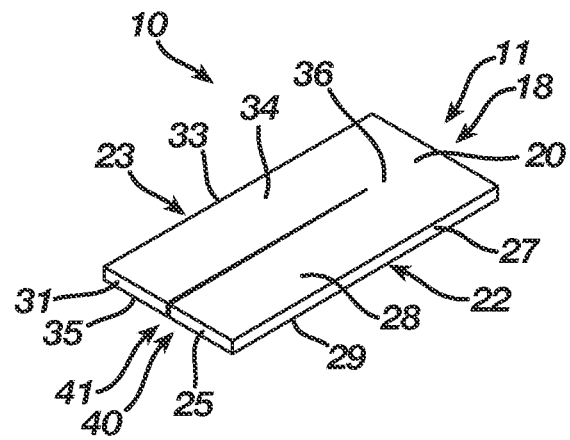
Figure 2C:
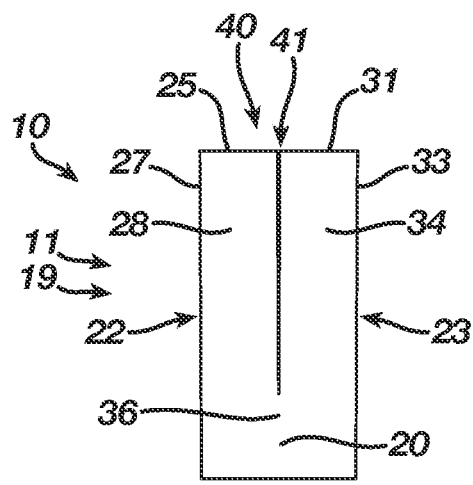
FIG. 2C is a top view illustrating the tension plate of the cerclage system transitioned to the insertion shape.
Figure 2D:
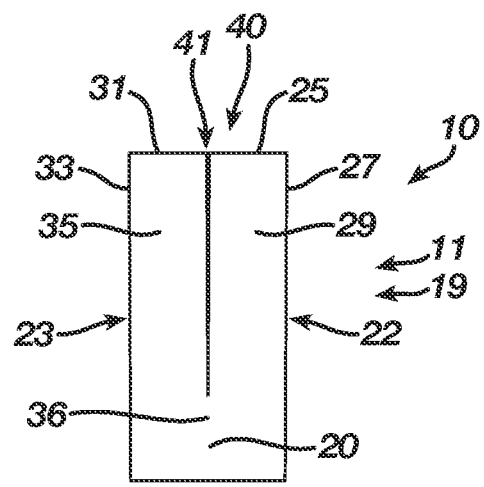
FIG. 2D is a bottom view illustrating the tension plate of the cerclage system transitioned to the insertion shape.

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

A cerclage system 10 as illustrated in FIGS. 1A-6C includes a tension plate 11 or a tension plate 12, a cerclage cable 13, and a cable lock 14. The cerclage system 10 as illustrated in FIGS. 7A-9C further includes a positioning pin 15 or a positioning pin 16 and a bone plate 17.

FIGS. 1A-1D and FIGS. 3A-3D, respectively, illustrate the tension plate 11 and the tension plate 12 in a natural shape 18, whereas FIGS. 2A-2D and FIGS. 4A-4D, respectively, illustrate the tension plate 11 and the tension plate 12 in an insertion shape 19. The tension plate 11 and the tension plate 12 may be manufactured from a shape memory material with superelastic or temperature dependent properties (e.g., Nitinol) such that the tension plate 11 and the tension plate 12 transition between the natural shape 18 and the insertion shape 19. The tension plate 11 and the tension plate 12 when deformed from the natural shape 18 to the insertion shape 19 store deliverable energy. In accordance with the manufacture of the tension plate 11 and the tension plate 12 from a shape memory material, the tension plate 11 and the tension plate 12 begin in the natural shape 18, are transitionable to the insertion shape 19, and, once deployed as part of the cerclage system 10, attempt to transition from the insertion shape 19 to the natural shape 18 whereby the tension plate 11 or the tension plate 12 deliver the energy stored therein. More particularly, as will be described further herein, the tension plate 11 and the tension plate 12 deliver the energy stored therein to the cerclage cable 13 such that the cerclage system 10 via the cerclage cable 13 affixes bone, bones, or bone pieces in order to promote a healing thereof. In the cerclage system 10, attempted transition of the tension plate 11 or the tension plate 12 from the insertion shape 19 to the natural shape 18 facilitates continuous compression of the bone, bones, or bone pieces in order to promote a fusion thereof.

The tension plate 11 includes a base 20 with a first arm 22 and a second arm 23 extending therefrom. The first arm 22 includes, a distal end 25, an interior side 26, an exterior side 27, a top surface 28, and a bottom surface 29. The second arm 23 includes a distal end 31, an interior side 32, an exterior side 33, a top surface 34, and a bottom surface 35. The base 20 proximate the first arm 22 adjacent the interior side 26 thereof and the second arm 23 adjacent the interior side 32 thereof includes a transition section 36. The tension plate 11 in a preferred embodiment is V-shaped, although one of ordinary skill in the art will recognize alternative shapes for the tension plate 11.

The natural shape 18 of the tension plate 11, as illustrated in FIGS. 1A-1D, involves the base 20 via the transition section 36 moving the first arm 22 and the second arm 23 to locate the first arm 22 and the second arm 23 in a natural position 37 whereby the first arm 22 at the interior side 26 and the second arm 23 at the interior side 32 expand to define a split 38 such that the first arm 22 at the distal end 25 and the second arm 23 at the distal end 31 are spaced apart at a first distance 39. Nevertheless, as illustrated in FIGS. 2A-2D, the tension plate 11 is deformable under the action of superelasticity or temperature dependent shape memory properties from the natural shape 18 to the insertion shape 19 where the base 20 via the transition section 36 deforms to store energy while also moving the first arm 22 and the second arm 23 to locate the first arm 22 and the second arm 23 in an insertion position 40 whereby the first arm 22 at the interior side 26 and the second arm 23 at the interior side 32 contract to reside adjacent thereby reducing the split 38 such that the first arm 22 at the distal end 25 and the second arm 23 at the distal end 31 are spaced apart at a second distance 41 that is less than the first distance 39. Since the insertion shape 19 is not the natural shape 18 of the tension plate 11, the tension plate 11 at the first arm 22 and the second arm 23 typically is mechanically constrained or the tension plate 11 is chilled until the tension plate 11 reaches its martensite phase whereby the base 20 via the transition section 36 once deformed maintains the first arm 22 and the second arm 23 in the insertion position 19. A release of a mechanical constraint or a heating of the tension plate 11 to the austenite phase allows the tension plate 11 via the base 20 to deliver the energy stored in the transition section 36 to the first arm 22 and the second arm 23 such that the first arm 22 and the second arm 23 attempt to move from the insertion position 40 to the natural position 37. As the first arm 22 and the second arm 23 attempt to expand, the first arm 22 and the second arm 23, as will be described further herein, exert a tensioning force upon the cerclage cable 13, resulting in the cerclage system 10 via the cerclage cable 13 continuously compressing bone, bones, or bone pieces, thereby affixing the bone, bones, or bone pieces in order to promote a fusion and a subsequent healing thereof. Mechanical constraints suitable to engage the tension plate 11 and maintain the tension plate 11 in the insertion shape 19 are available from DePuy Synthes Products, Inc., 325 Paramount Drive, Rayham, MA 02767, and include forceps, pliers, and like devices.

The tension plate 12 is substantially similar in design and operation relative to the tension plate 11 such that, for the sake of brevity, only differences therebetween will be described herein. Moreover, one of ordinary skill in the art will recognize that like parts of the tension plate 12 labeled with like numerals of the tension plate 11 incorporate a design and function as previously set forth in the detailed description of the tension plate 11. The tension plate 12 differs from the tension plate 11 in that the tension plate 12 in the first arm 22 includes a first aperture 42, a second aperture 43, and a third aperture 44 therethrough. In a preferred embodiment of the tension plate 12, the first arm 22 includes the first aperture 42 located adjacent the base 20 of the tension plate 12, the second aperture 43 located adjacent the distal end 25 of the first arm 22, and the third aperture 44 located centrally relative to the first arm 22; although one of ordinary skill in the art will recognize the third aperture 44 may be located at any point along the first arm 22 between the first aperture 42 and the second aperture 43.

In the preferred embodiment of the tension plate 12, the first aperture 42 and the second aperture 43 are configured to secure the tension plate 12 with bone, bones, or bone pieces using a suitable fixation device such as a biocompatible locking, non-locking, or self-tapping bone screw in order to prevent disengagement of the tension plate 12 from the bone, bones, or bone pieces, whereas the third aperture 44 is configured to facilitate a securing of the cerclage cable 13 with the tension plate 12 in order to prevent disengagement of the cerclage cable 13 from the tension plate 12 during an exertion of a tensioning force upon the cerclage cable 13 by the tension plate 12. Illustratively, the cerclage cable 13 inserts through the third aperture 44 or the cerclage cable 13 inserts through either the positioning pin 15 or the positioning pin 16 which has been coupled with the third aperture 44. In the alternative, one of ordinary skill in the art will recognize that the first aperture 42 and the third aperture 44 are configured to secure the tension plate 12 with bone, bones, or bone pieces, whereas the second aperture 43 is configured to facilitate a securing of the cerclage cable 13 with the tension plate 12, or the second aperture 43 and the third aperture 44 are configured to secure the tension plate 12 with bone, bones, or bone pieces, whereas the first aperture 42 is configured to facilitate a securing of the cerclage cable 13 with the tension plate 12. The first aperture 42, the second aperture 43, and the third aperture 44 may be apertures including smooth bores, apertures including threads for engagement with a bone screw or the positioning pin 16, or any combination thereof.

While the tension plate 11 does not include apertures and the tension plate 12 in the preferred embodiment includes the first aperture 42, the second aperture 43, and the third aperture 44, one of ordinary skill in the art will recognize the tension plate 12 may include any one of the first aperture 42, the second aperture 43, and the third aperture 44 or any two of the first aperture 42, the second aperture 43, and the third aperture 44. In a configuration with one of the first aperture 42, the second aperture 43, and the third aperture 44, the single aperture may be used either to secure the tension plate 12 with bone, bones, or bone pieces or to facilitate a securing of the cerclage cable 13 with the tension plate 12. In a configuration with two of the first aperture 42, the second aperture 43, and the third aperture 44, a first aperture may be used to secure the tension plate 12 with bone, bones, or bone pieces, whereas a second aperture may be used to facilitate a securing of the cerclage cable 13 with the tension plate 12. Although the tension plate 12 includes the first aperture 42, the second aperture 43, and the third aperture 44 in the first arm 22, one of ordinary skill in the art will recognize the first aperture 42, the second aperture 43, and the third aperture 44 are transferable to the second arm 23.

Figure 5:
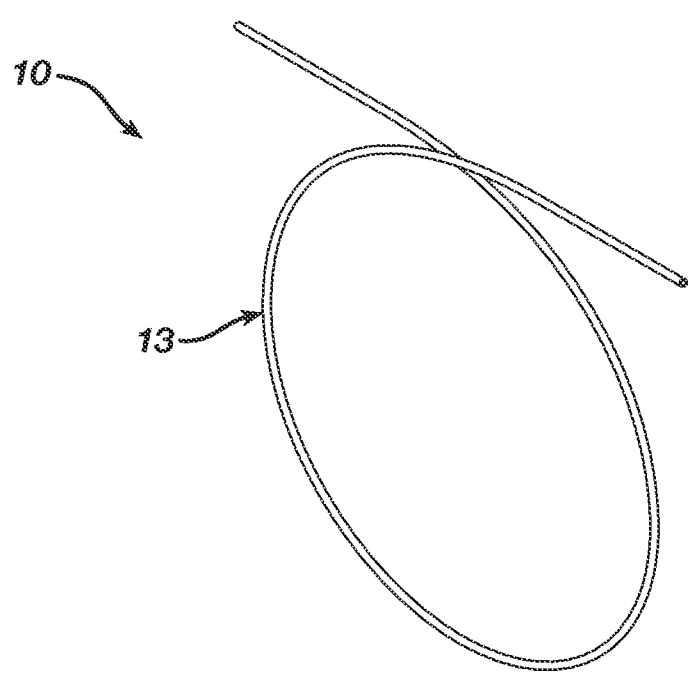
FIG. 5 is an isometric view illustrating a cerclage cable of the cerclage system.

FIG. 5 illustrates a cerclage cable which is presented herein as an example of the cerclage cable 13 suitable for implementation in the cerclage system 10. The cerclage cable 13 includes a length as necessary to encircle bone, bones, or bone pieces such that the cerclage system 10 via the cerclage cable 13 affixes the bone, bones, or bone pieces in order to promote a fusion and a subsequent healing thereof. Cerclage cables suitable for incorporation and use in the cerclage system 10 are available from DePuy Synthes Products, Inc., 325 Paramount Drive, Rayham, MA 02767.

Figure 6A:
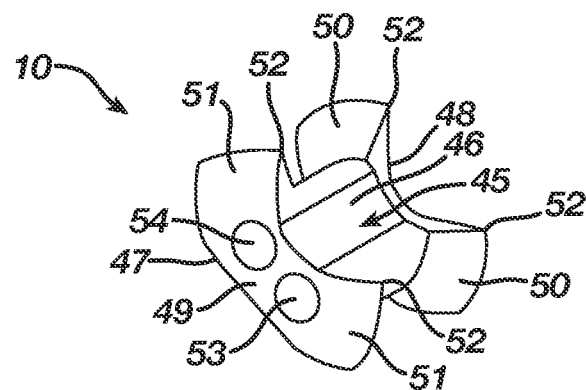
FIG. 6A is an isometric view illustrating a cable lock of the cerclage system.
Figure 6B:
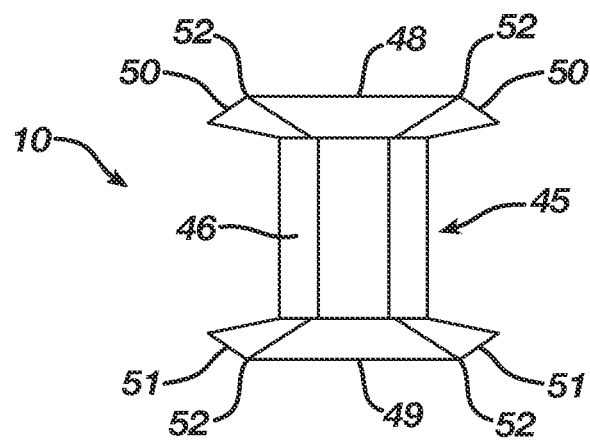
FIG. 6B is a front view illustrating the cable lock of the cerclage system.
Figure 6C:
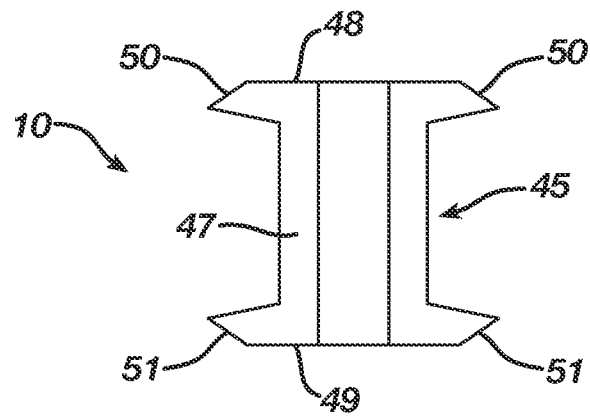
FIG. 6C is a rear view illustrating the cable lock of the cerclage system.

FIGS. 6A-6C illustrate a cable lock which is presented herein as an example of the cable lock 14 suitable for implementation in the cerclage system 10. The cable lock 14 includes a body 45 with a front 46 configured to face bone, bones, or bone pieces, a rear 47, a top 48, and a bottom 49. The body 45 includes wings 50 extending therefrom at the top 48 and wings 51 extending therefrom at the bottom 49. The wings 50 and 51 each include a gripping point 52 configured when necessary to engage bone, bones, or bone pieces thereby preventing slippage of the cable lock 14 relative to the bone, bones, or bone pieces. The cable lock 14 includes a first bore 53 and a second bore 54 extending through the body 45 from the top 48 to the bottom 49. The first bore 53 and the second bore 54 are configured to receive therethrough the cerclage cable 13 in order to facilitate a coupling of the cable lock 14 with the cerclage cable 13. The cable lock 14 is manufactured from any biocompatible metal or metal alloy suitable for crimping, such as, for example, titanium, stainless steel, titanium alloy, and cobalt chrome alloy. After insertion of the cerclage cable 13 through the first bore 53 and the second bore 54, the cable lock 14 is crimped resulting in the cable lock 14 mechanically engaging the cerclage cable 13 and thus locking the cerclage cable 13 about bone, bones, or bone pieces. In accordance therewith, the cerclage system 10 via the cerclage cable 13 affixes the bone, bones, or bone pieces in order to promote a fusion and a subsequent healing thereof. Cable locks suitable for incorporation and use in the cerclage system 10 are available from DePuy Synthes Products, Inc., 325 Paramount Drive, Rayham, MA 02767.

Figure 7A:
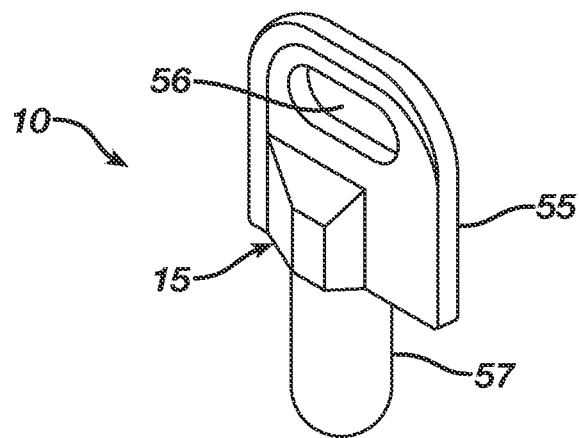
FIG. 7A is an isometric view illustrating a positioning pin of the cerclage system.
Figure 7B:
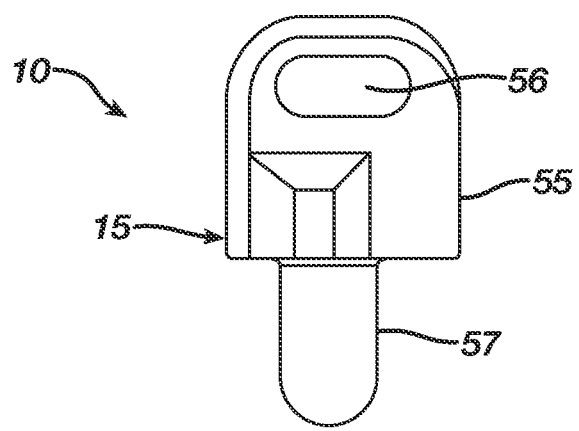
FIG. 7B is a front view illustrating the positioning pin of the cerclage system.

FIGS. 7A-7B illustrate a positioning pin which is presented herein as an example of the positioning pin 15 suitable for implementation in the cerclage system 10. The positioning pin 15 includes a head 55 defining an aperture 56 therethrough formed integrally with a shaft 57. In the preferred embodiment of the positioning pin 15, the shaft 57 is configured to fit within the third aperture 44 of the tension plate 12 and frictionally engage the third aperture 44 such that the positioning pin 15 connects with the tension plate 12. The aperture 56 is configured to receive the cerclage cable 13 therethrough whereby the positioning pin 15 via the fitting of the shaft 57 into the third aperture 44 and the insertion of the cerclage cable 13 through the aperture 56 of the head 55 secures the cerclage cable 13 with the tension plate 12 in order to prevent disengagement of the cerclage cable 13 from the tension plate 12 during an exertion of a tensioning force upon the cerclage cable 13 by the tension plate 12. While the shaft 57 in the preferred embodiment inserts into the third aperture 44, one of ordinary skill in the art will recognize the shaft 57 fits into either the first aperture 42 or the second aperture 43 to connect the positioning pin 15 with the tension plate 12. The positioning pin 15 as will be described more fully herein is configured to connect with the bone plate 17 to facilitate a securing of the cerclage cable 13 with the bone plate 17. Positioning pins suitable for incorporation and use in the cerclage system 10 are available from DePuy Synthes Products, Inc., 325 Paramount Drive, Rayham, MA 02767.

Figure 8A:
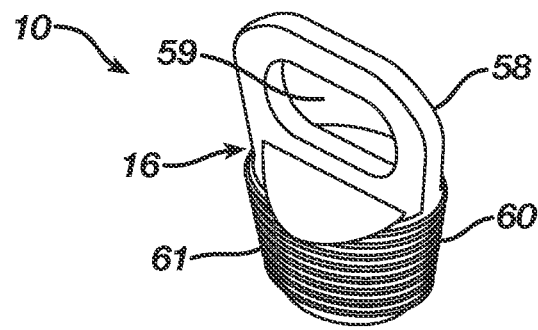
FIG. 8A is an isometric view illustrating an alternative of the positioning pin of the cerclage system.
Figure 8B:
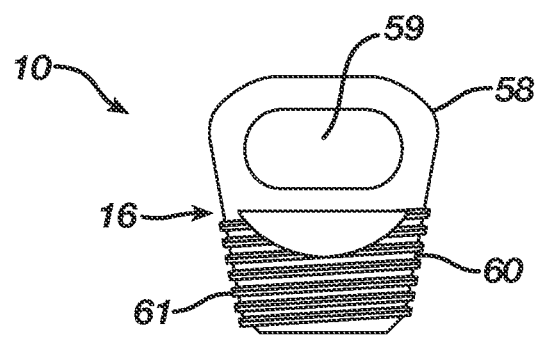
FIG. 8B is a front view illustrating the alternative positioning pin of the cerclage system.

FIGS. 8A-8B illustrate a positioning pin which is presented herein as an example of the positioning pin 16 suitable for implementation in the cerclage system 10. The positioning pin 16 includes a head 58 defining an aperture 59 therethrough formed integrally with a shaft 60. In the preferred embodiment of the positioning pin 16, the shaft 60 includes threads 61 that facilitate connection of the positioning pin 16 with the tension plate 12. More particularly, when the third aperture 44 of the tension plate 12 includes threads, the shaft 60 is configured to fit within the third aperture 44 and engage the third aperture 44 via the threads 61 such that the positioning pin 16 connects with the tension plate 12. The aperture 59 is configured to receive the cerclage cable 13 therethrough whereby the positioning pin 16 via the threading of the shaft 60 into the third aperture 44 and the insertion of the cerclage cable 13 through the aperture 59 of the head 58 secures the cerclage cable 13 with the tension plate 12 in order to prevent disengagement of the cerclage cable 13 from the tension plate 12 during an exertion of a tensioning force upon the cerclage cable 13 by the tension plate 12. While the shaft 60 via the threads 61 in the preferred embodiment threads into the third aperture 44, one of ordinary skill in the art will recognize the shaft 60 threads into either the first aperture 42 or the second aperture 43 to connect the positioning pin 16 with the tension plate 12. The positioning pin 16 as will be described more fully herein is configured to connect with the bone plate 17 to facilitate a securing of the cerclage cable 13 with the bone plate 17. Positioning pins suitable for incorporation and use in the cerclage system 10 are available from DePuy Synthes Products, Inc., 325 Paramount Drive, Rayham, MA 02767.

Figure 9A:
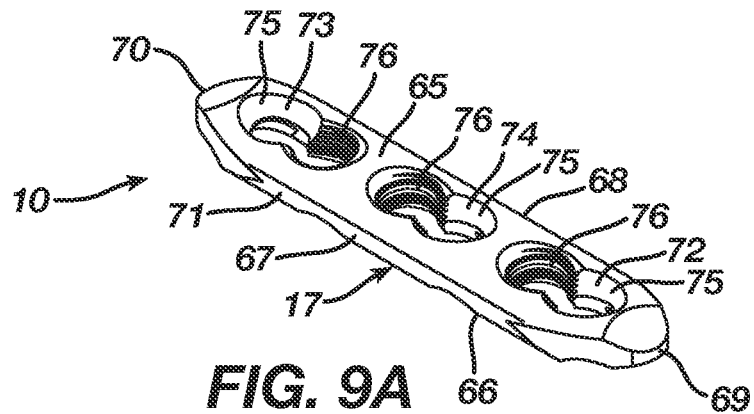
FIG. 9A is an isometric view illustrating a bone plate of the cerclage system.
Figure 9B:
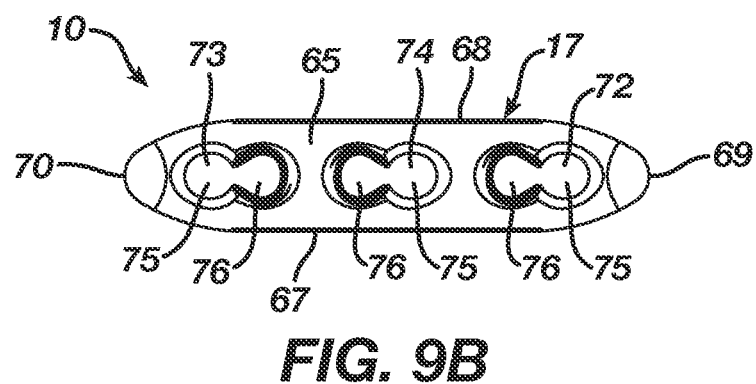
FIG. 9B is a top view illustrating the bone plate of the cerclage system.
Figure 9C:
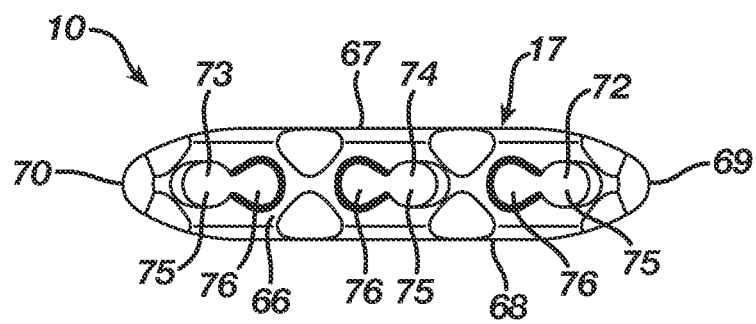
FIG. 9C is a bottom view illustrating the bone plate of the cerclage system.

FIGS. 9A-9C illustrate a bone plate which is presented herein as an example of the bone plate 17 suitable for implementation in the cerclage system 10. The bone plate 17 exhibits a three-dimensional form having a length, width, and height, and, in particular, the bone plate 17 includes an upper surface 65 and a lower surface 66 with first and second sides 67 and 68 and first and second ends 69 and 70 therebetween. The upper surface 65 and the lower surface 66 define a height 71 that provides strength to the bone plate 17 while a contouring of the upper surface 65 presents the bone plate 17 with a lowest possible profile. The lower surface 66 is substantially flat in order for the bone plate 17 at the lower surface 66 to seat flush atop bone, bones, or bone pieces.

The bone plate 17 includes at least a first opening 72 at the first end 69 extending therethrough from the upper surface 65 to the lower surface 66, a second opening 73 at the second end 70 extending therethrough from the upper surface 65 to the lower surface 66, and a third opening 74 between the first opening 72 and the second opening 73 extending therethrough from the upper surface 65 to the lower surface 66. The bone plate 17 includes the first opening 72, the second opening 73, and the third opening 74 in order for the bone plate 17 to receive therethrough either a fixation device, such as a biocompatible locking, non-locking, or self-tapping bone screw, or one of the positioning pin 15 and the positioning pin 16. The first opening 72, the second opening 73, and the third opening 74 in the preferred embodiment each include an oblong shape that produces a first aperture 75 opposed to a second aperture 76. The first apertures 75 include a smooth bore that facilitates insertion of the positioning pin 15, whereas the second apertures 76 includes a threaded bore that facilitates insertion of the positioning pin 16 or a fixation device.

While a securing of the bone plate 17 with bone, bones, or bone pieces and with the cerclage cable 13 using one of the positioning pin 15 and the positioning pin 16 requires only the first, second, and third apertures 72-74, one of ordinary skill in the art will recognize the bone plate 17 may include additional openings that receive a fixation device for a further securing of the bone plate 17 with the bone, bones, or bone pieces or one of the positioning pin 15 and the positioning pin 16 for a further securing of the bone plate 17 with the cerclage cable 13. Moreover, although the bone plate 17 is illustrated as an elongated linear plate, one of ordinary skill in the art will recognize alternative shapes for the bone plate 17, such as, for example, H-shaped plates, X-shaped plates, and the like.

The bone plate 17 in the preferred embodiment may be manufactured from any biocompatible metal or metal alloy, such as, for example, titanium, stainless steel, titanium alloy, and cobalt chrome alloy. Nevertheless, one of ordinary skill in the art will recognize the bone plate 17 may be manufactured from a shape memory material with superelastic or temperature dependent properties (e.g., Nitinol) such that the bone plate 17 transitions between a natural shape and the insertion shape. The bone plate 17 when deformed from the natural shape to the insertion shape stores energy deliverable to bone, bones, or bone pieces. In accordance with its manufacture from shape memory material, the bone plate 17 begins in the natural shape, is transitionable to the insertion shape, and, once implanted in bone, bones, or bone pieces, attempts to transition from the insertion shape to the natural shape whereby the bone plate 17 delivers the energy stored therein to the bone, bones, or bone pieces in order to affix the bone, bones, or bone pieces and promote a healing thereof. In a shape memory material embodiment of the bone plate 17, attempted transition of the bone plate 17 from the insertion shape to the natural shape continuously compresses the bone, bones, or bone pieces to promote fusion thereof. Bone plates suitable for incorporation and use in the cerclage system 10 are available from DePuy Synthes Products, Inc., 325 Paramount Drive, Rayham, MA 02767.

Figure 10A:
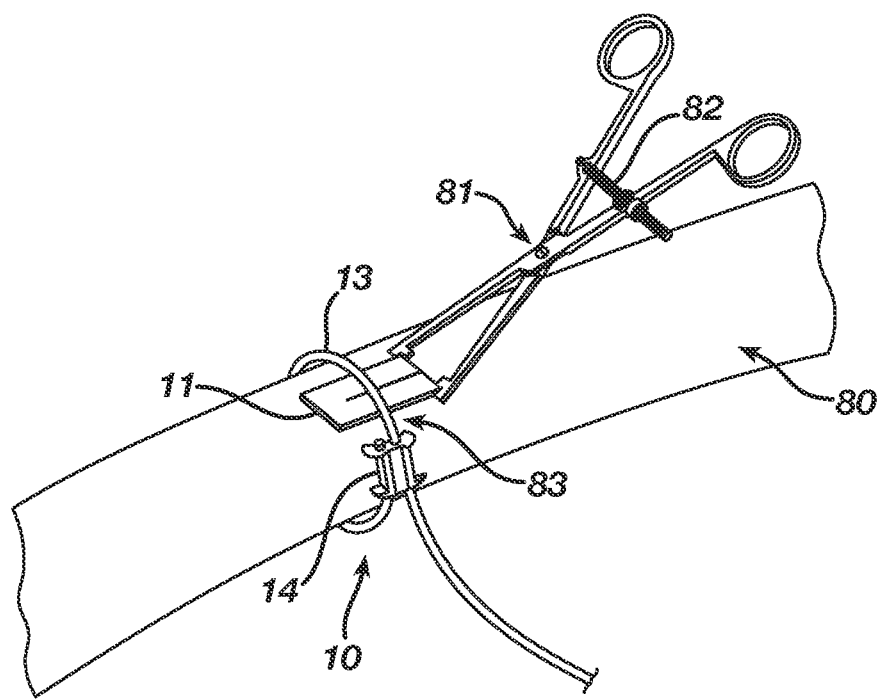
FIGS. 10A-12 are isometric views illustrating use of the cerclage system to affix bone, bones, or bone pieces.
Figure 10B:
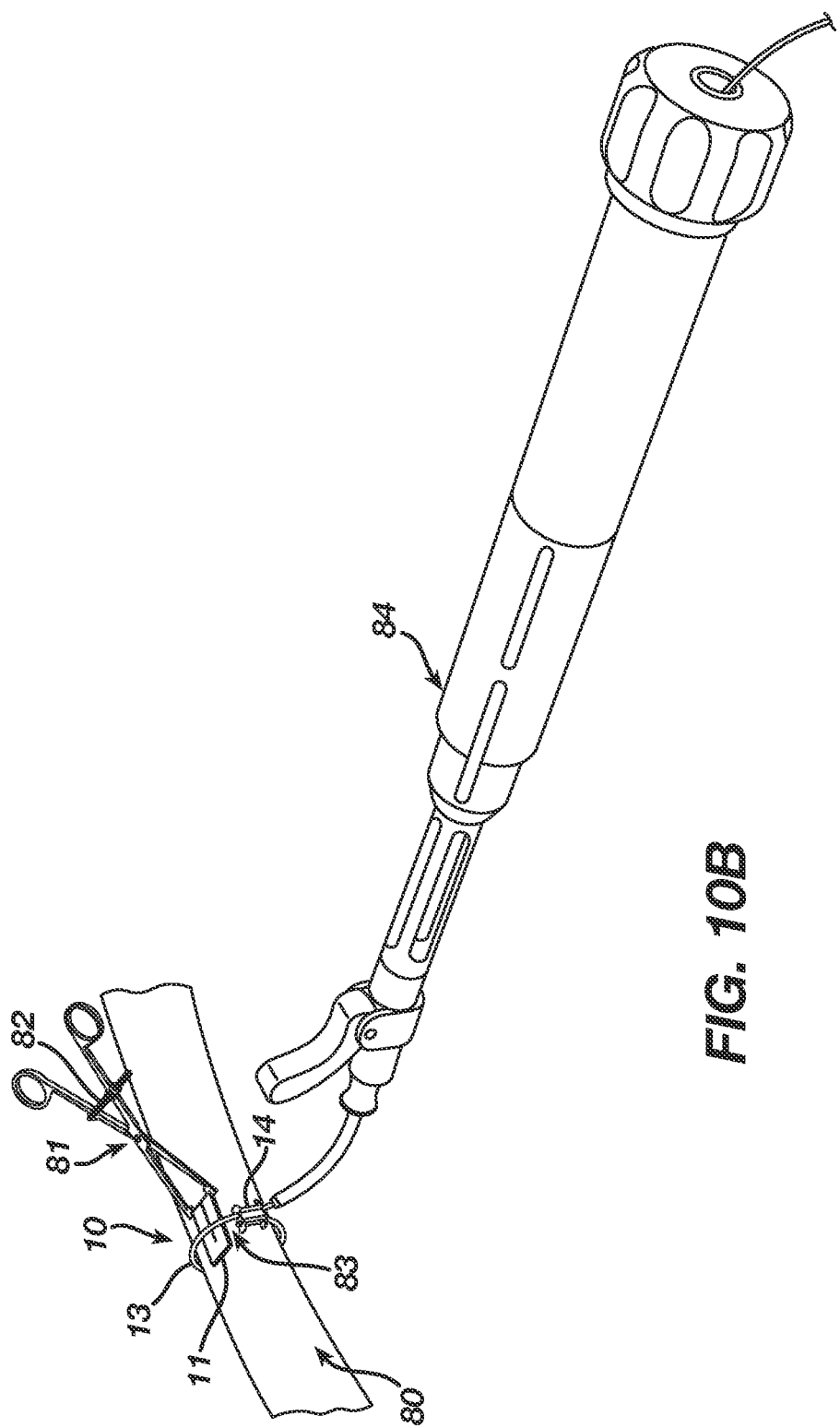
Figure 10C:
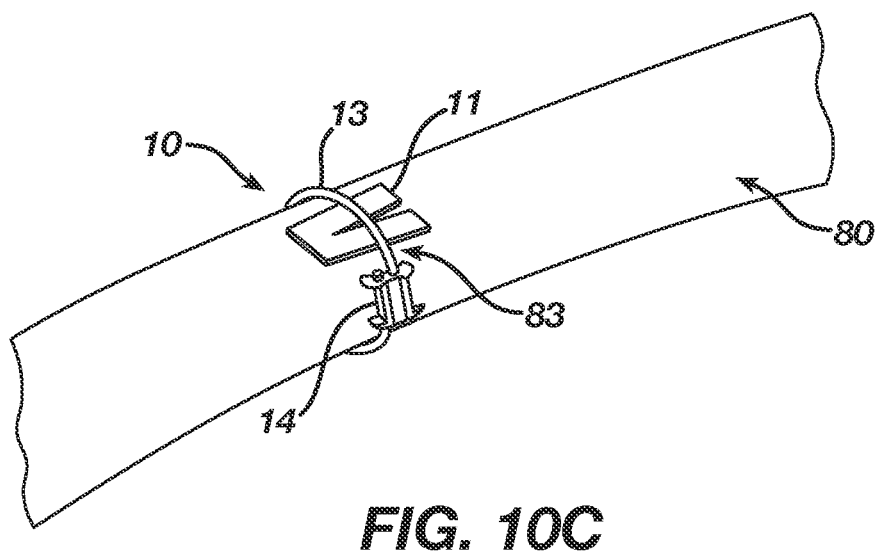

FIGS. 10A-10C illustrate use of the cerclage system 10 to affix bone, bones, or bone pieces, and, in particular, use of the cerclage system 10 to affix a bone 80, which is presented herein as an example bone having experienced a break, fracture, crack, or the like. Use of the cerclage system 10 includes a mechanical deformation of the tension plate 11 from the natural shape 18 to the insertion shape 19 where the transition plate 11 stores deliverable energy followed by a constraining of the tension plate 11 in the insertion shape 19 utilizing a suitable mechanical constraint. Illustratively, forceps 81, which are presented herein as an example mechanical constraint, engage the tension plate 11 and constrain the tension plate 11 in the insertion shape 19. The forceps 81 include a locking system 82 in order to mechanically retain the tension plate 11 in the insertion shape 19, such as, for example, the depicted screw and nut drive system, a ratchet system, or the like.

Referring to FIG. 10A, a surgeon aligns the bone 80 at a fusion zone 83 in an orientation that promotes fixation of the bone 80 and a proper healing thereof. After aligning the bone 80, the surgeon utilizing the forceps 81 positions the tension plate 11 in the insertion shape 19 atop the bone 80 across the fixation zone 83 with the base 20 of the tension plate 11 adjacent a first side of the fixation zone 83 and the distal end 25 of the first arm 22 and the distal end 31 of the second arm 23 adjacent a second side of the fixation zone 83. The surgeon inserts a first end of the cerclage cable 13 into the cable lock 14 via the first bore 53 thereof. The surgeon aligns the cable lock 14 relative to the tension plate 11 and then places the cable lock 14 atop the bone 80 oriented with the front 46 thereof facing the bone 80. The surgeon encircles the bone 80 at the fixation zone 83 with the cerclage cable 13 such that the cerclage cable 13 passes over the tension plate 11. The surgeon if desired may utilize a cable passer, which is a known surgical instrument available from DePuy Synthes Products, Inc., 325 Paramount Drive, Rayham, MA 02767, to assist in encircling the bone 80. Upon encircling the bone 80 at the fixation zone 83 with the cerclage cable 13, the surgeon inserts a second end of the cerclage cable 13 into the cable lock 14 via the second bore 54 thereof.

Referring to FIG. 10B, the surgeon, after passing the second end of the cerclage cable 13 through the cable lock 14 via the second bore 54 thereof, inserts the second end of the cerclage cable 13 through a cable tensioner 84, which is a known surgical instrument available from DePuy Synthes Products, Inc., 325 Paramount Drive, Rayham, MA 02767. The surgeon manipulates the cable tensioner 84 to tension the cerclage cable 13 until the cerclage cable 13 abuts the bone 80 while securing the tension plate 11 atop the bone 80. The surgeon utilizes a cable lock crimper, which is a known surgical instrument available from DePuy Synthes Products, Inc., 325 Paramount Drive, Rayham, MA 02767, in order to crimp the cable lock 14. The crimping of the cable lock 14 locks the cerclage cable 13 within the cable lock 14 such that the cerclage cable 13 remains secured about the bone 80 at the fixation zone 83 while holding the tension plate 11 atop the bone 80 across the fixation zone 83. After removing the cerclage cable 13 from the cable tensioner 84, the surgeon, utilizing a cable cutter, which is a known surgical instrument available from DePuy Synthes Products, Inc., 325 Paramount Drive, Rayham, MA 02767, cuts the cerclage cable 13 at the second bore 54 of the cable lock 14.

Referring to FIG. 10C, the surgeon manipulates the locking system 82 of the forceps 81 in order to release the tension plate 11 from the forceps 81. Upon removal of the forceps 81 from the tension plate 11, the tension plate 11 attempts to transition from the insertion shape 19 to the natural shape 18. As the tension plate 11 attempts transition from the insertion shape 19 to the natural shape 18, the tension plate 11 via the engagement thereof with the cerclage cable 13 delivers the energy stored therein to the cerclage cable 13. More particularly, the base 20 via the transition section 36, which stores the deliverable energy, attempts to move the first arm 22 and the second arm 23 from the insertion position 40 to the natural position 37. In accordance therewith, the first arm 22 and the second arm 23 attempt to expand such that the first arm 22 and the second arm 23, via the engagement of the first arm 22 with the cerclage cable 13 at the exterior side 27 thereof and the engagement of the second arm 23 with the cerclage cable 13 at the exterior side 33 thereof, exert a tensioning force upon the cerclage cable 13. This tensioning force exerted upon the cerclage cable 13 by the first arm 22 and the second arm 23 results in the cerclage system 10 via the tensioning of the cerclage cable 13 about the bone 80 at the fixation zone 83 thereof continuously compressing the bone 80, thereby affixing the bone 80 in order to promote a fusion and a subsequent healing thereof.

Figure 11A:
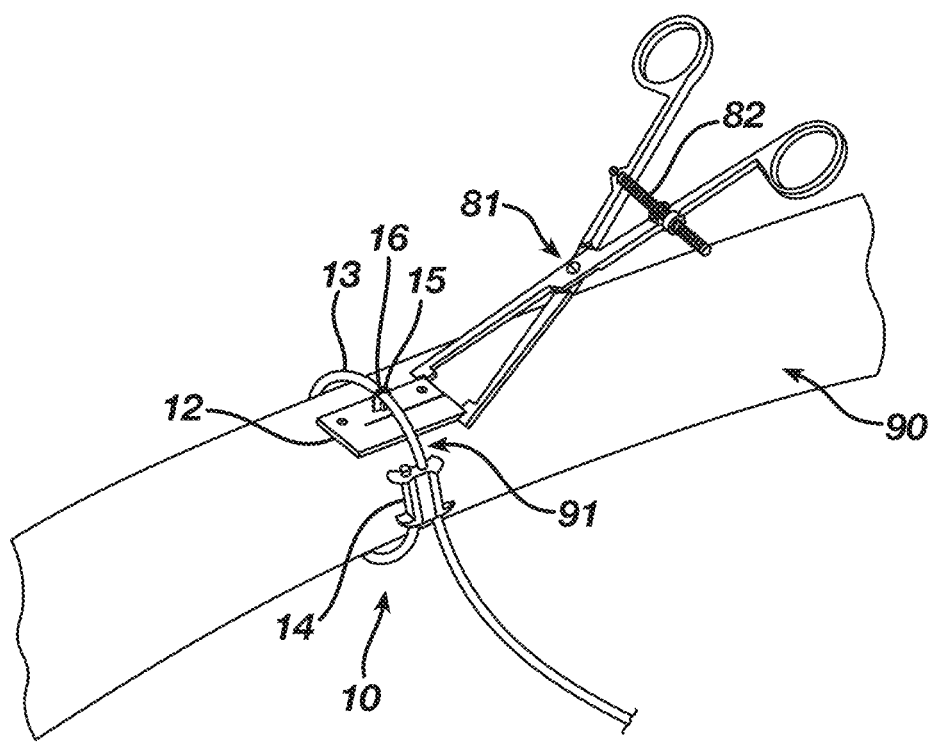
Figure 11B:
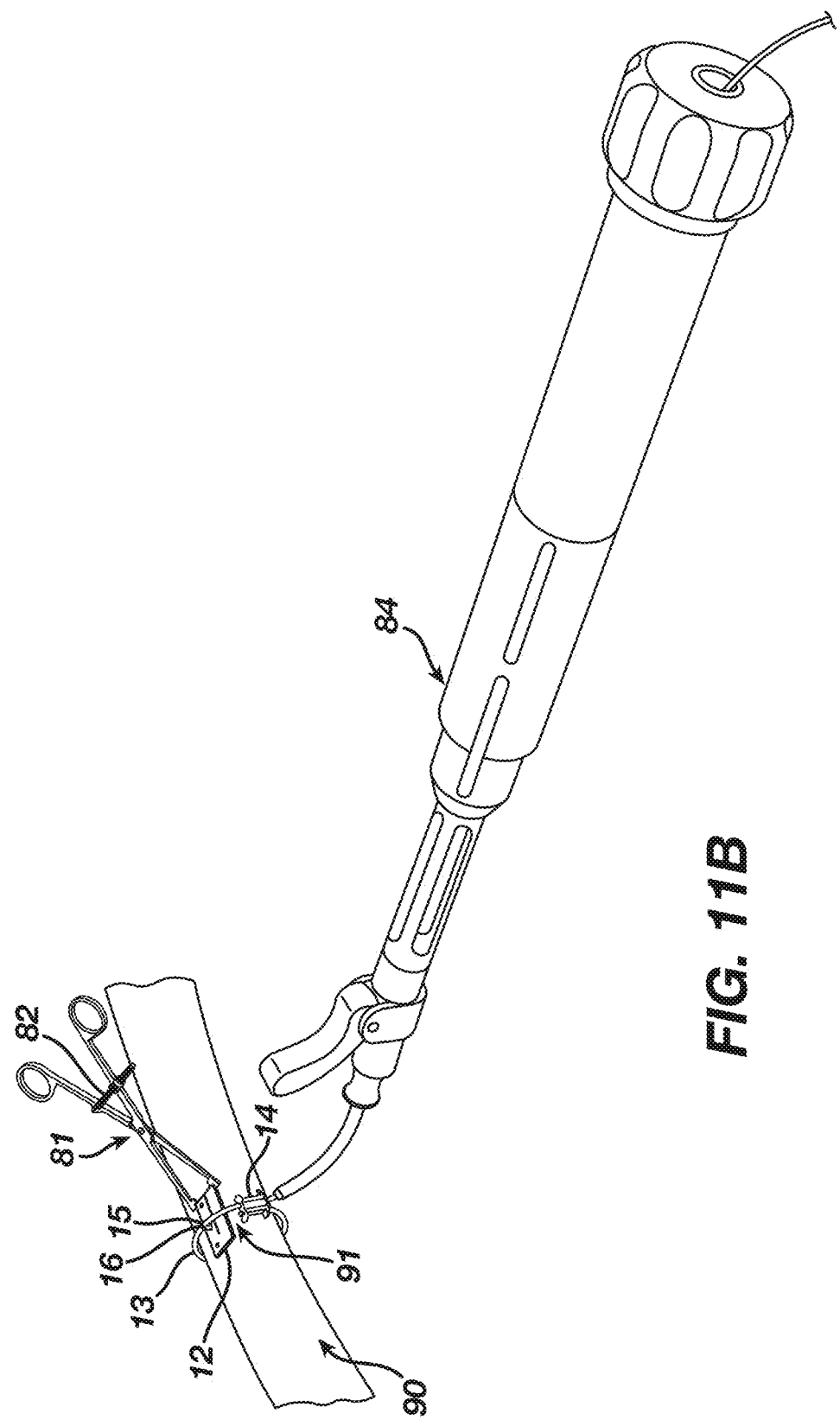
Figure 11C:
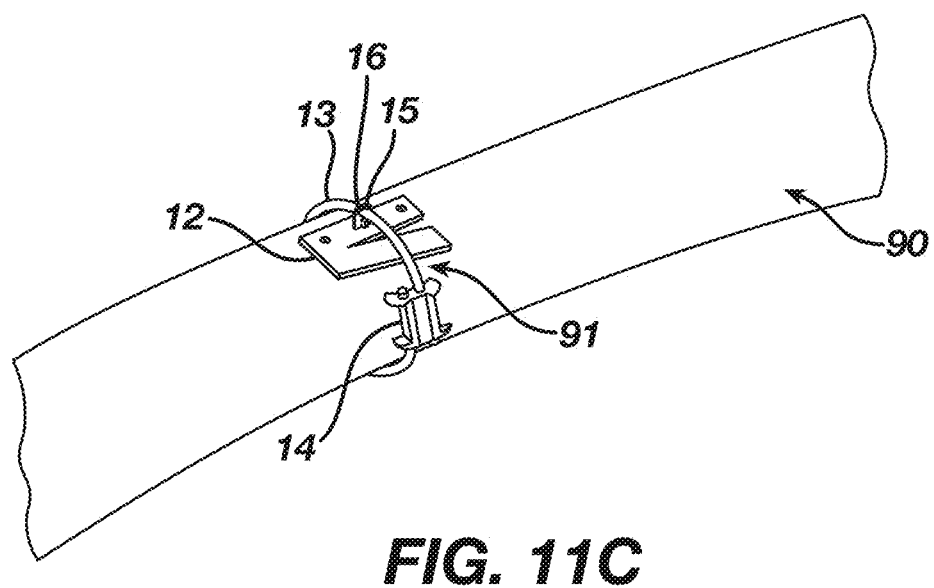

FIGS. 11A-11C illustrate use of the cerclage system 10 to affix bone, bones, or bone pieces, and, in particular, use of the cerclage system 10 to affix a bone 90, which is presented herein as an example bone having experienced a break, fracture, crack, or the like. Use of the cerclage system 10 further includes a mechanical deformation of the tension plate 12 from the natural shape 18 to the insertion shape 19 where the transition plate 12 stores deliverable energy followed by a constraining of the tension plate 12 in the insertion shape 19 utilizing a suitable mechanical constraint. Illustratively, forceps 81, which are presented herein as an example mechanical constraint, engage the tension plate 12 and constrain the tension plate 12 in the insertion shape 19. The forceps 81 include a locking system 82 in order to mechanically retain the tension plate 12 in the insertion shape 19, such as, for example, the depicted screw and nut drive system, a ratchet system, or the like.

Referring to FIG. 11A, either before or after deformation of the tension plate 12, a positioning pin 15 connects with the tension plate 12 via a fitting of the shaft 57 thereof into the third aperture 44 of the tension plate 12. Alternatively, if the third aperture 44 includes threads, a positioning pin 16 connects with the tension plate 12 via a threading of the shaft 60 thereof into the third aperture 44 of the tension plate 12. A surgeon aligns the bone 90 at a fusion zone 91 in an orientation that promotes fixation of the bone 90 and a proper healing thereof. After aligning the bone 90, the surgeon utilizing the forceps 81 positions the tension plate 12 in the insertion shape 19 atop the bone 90 across the fixation zone 91 with the positioning pin 15 aligned with the fixation zone 91, the base 20 of the tension plate 12 adjacent a first side of the fixation zone 91, and the distal end 25 of the first arm 22 and the distal end 31 of the second arm 23 adjacent a second side of the fixation zone 91. The surgeon inserts a first bone screw through the first aperture 42 and into the bone 90 and a second bone screw through the second aperture 43 and into the bone 90 in order to prevent disengagement of the tension plate 12 from the bone 90. The surgeon inserts a first end of the cerclage cable 13 into the cable lock 14 via the first bore 53 thereof. The surgeon aligns the cable lock 14 relative to the tension plate 12 and then places the cable lock 14 atop the bone 90 oriented with the front 46 thereof facing the bone 90. The surgeon encircles the bone 90 at the fixation zone 91 with the cerclage cable 13 while also passing the cerclage cable 13 through the aperture 56 of the head 55 for the positioning pin 15. The insertion of the cerclage cable 13 through the aperture 56 in the positioning pin 15 secures the cerclage cable 13 with the tension plate 12 thereby preventing a disengagement of the cerclage cable 13 from the tension plate 12 during an exertion of a tensioning force upon the cerclage cable 13 by the tension plate 12. The surgeon if desired may utilize a cable passer, which is a known surgical instrument available from DePuy Synthes Products, Inc., 325 Paramount Drive, Rayham, MA 02767, to assist in encircling the bone 90. Upon encircling the bone 90 at the fixation zone 91 with the cerclage cable 13 including inserting the cerclage cable 13 through the aperture 56 of the positioning pin 15, the surgeon inserts a second end of the cerclage cable 13 into the cable lock 14 via the second bore 54 thereof.

Referring to FIG. 11B, the surgeon, after passing the second end of the cerclage cable 13 through the cable lock 14 via the second bore 54 thereof, inserts the second end of the cerclage cable 13 through a cable tensioner 84, which is a known surgical instrument available from DePuy Synthes Products, Inc., 325 Paramount Drive, Rayham, MA 02767. The surgeon manipulates the cable tensioner 84 to tension the cerclage cable 13 until the cerclage cable 13 abuts the bone 90 while remaining secured atop the tension plate 12 via the positioning pin 15. The surgeon utilizes a cable lock crimper, which is a known surgical instrument available from DePuy Synthes Products, Inc., 325 Paramount Drive, Rayham, MA 02767, in order to crimp the cable lock 14. The crimping of the cable lock 14 locks the cerclage cable 13 within the cable lock 14 such that the cerclage cable 13 remains secured about the bone 90 at the fixation zone 91 while remaining held atop the tension plate 12 by the positioning pin 15. After removing the cerclage cable 13 from the cable tensioner 84, the surgeon, utilizing a cable cutter, which is a known surgical instrument available from DePuy Synthes Products, Inc., 325 Paramount Drive, Rayham, MA 02767, cuts the cerclage cable 13 at the second bore 54 of the cable lock 14.

Referring to FIG. 11C, the surgeon manipulates the locking system 82 of the forceps 81 in order to release the tension plate 12 from the forceps 81. Upon removal of the forceps 81 from the tension plate 12, the tension plate 12 attempts to transition from the insertion shape 19 to the natural shape 18. As the tension plate 12 attempts transition from the insertion shape 19 to the natural shape 18, the tension plate 12 via the engagement thereof with the cerclage cable 13 delivers the energy stored therein to the cerclage cable 13. More particularly, the base 20 via the transition section 36, which stores the deliverable energy, attempts to move the first arm 22 and the second arm 23 from the insertion position 40 to the natural position 37. In accordance therewith, the second arm 23, due to the securing of the first arm 22 with the bone 90 across the fixation zone 91, attempts to expand from the first arm 22 such that the second arm 23, via the engagement of the first arm 22 with the cerclage cable 13 utilizing the positioning pin 15 and the engagement of the second arm 23 with the cerclage cable 13 at the exterior side 33 thereof, exerts a tensioning force upon the cerclage cable 13. This tensioning force exerted upon the cerclage cable 13 by the second arm 23 results in the cerclage system 10 via the tensioning of the cerclage cable 13 about the bone 90 at the fixation zone 91 thereof continuously compressing the bone 90, thereby affixing the bone 90 in order to promote a fusion and a subsequent healing thereof.

Although FIGS. 11A-11C illustrate use of a tension plate 12 including the first aperture 42, the second aperture 43, and the third aperture 44, one of ordinary skill in the art will recognize alternative uses and configurations for the tension plate 12. Illustratively, the positioning pin 15 or the positioning pin 16 may be connected with the tension plate 12 using the first aperture 42 or the second aperture 43 while the third aperture 44 is utilized to secure the tension plate 12 with the bone 90 via a bone screw. Additionally, a single aperture in the tension plate 12 may be used to connect the tension plate 12 with the positioning pin 15 or the positioning pin 16 or the single aperture may be used to secure the tension plate 12 with the bone 90 via a bone screw. Moreover, two apertures in the tension plate 12 may be used whereby a first aperture connects the tension plate 12 with the positioning pin 15 or the positioning pin 16 and a second aperture secures the tension plate 12 with the bone 90 via a bone screw.

Figure 12:
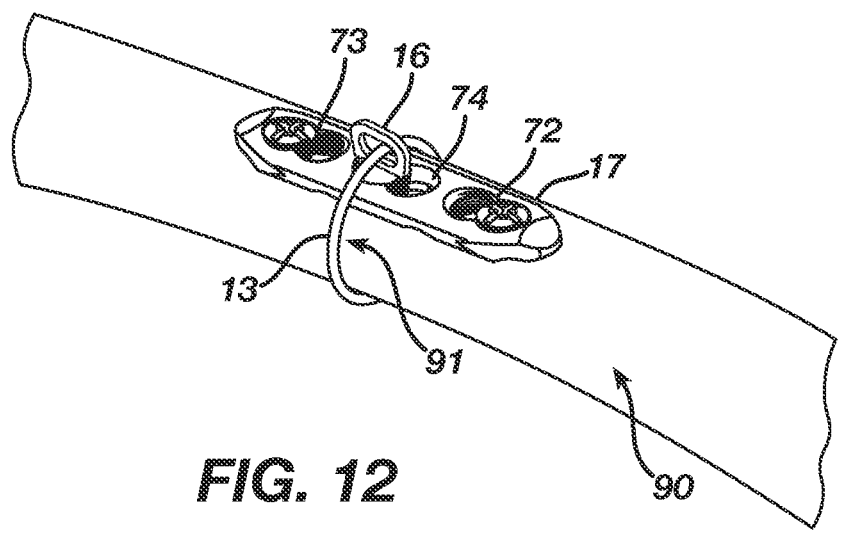

FIG. 12 illustrates use of the cerclage system 10 to affix bone, bones, or bone pieces, and, in particular, use of the cerclage system 10, which includes the bone plate 17, to affix the bone 80 or the bone 90, which is presented herein as an example. A positioning pin 16 connects with the bone plate 17 via a threading of the shaft 60 thereof into the second aperture 76 of the third opening 74 for the bone plate 17. Alternatively, a positioning pin 15 connects with the bone plate 17 via a fitting of the shaft 57 thereof into the first aperture 75 of the third opening 74 for the bone plate 17. After aligning the bone 90 at the fusion zone 91 but prior to the positioning of the tension plate 12 atop the bone 90 and the encircling of the bone 90 at the fixation zone 91 with the cerclage cable 13, the surgeon affixes the bone plate 17 atop the bone 90 at a desired location spaced apart from the tension plate 12 that promotes fusion of the bone 90 and a subsequent healing thereof. More particularly, the surgeon positions the bone plate 17 atop the bone 90 across the fixation zone 91 with the positioning pin 16 aligned with the fixation zone 91 and with the first opening 72 of the bone plate 17 adjacent a first side of the fixation zone 91 and the second opening 73 of bone plate 17 adjacent a second side of the fixation zone 91. The surgeon inserts a first bone screw through the first opening 72 via either the first aperture 75 or the second aperture 76 and into the bone 90 and a second bone screw through the second opening 73 via either the first aperture 75 or the second aperture 76 and into the bone 90 in order to prevent disengagement of the bone plate 17 from the bone 90. During the encircling of the bone 90 at the fixation zone 91 with the cerclage cable 13, the surgeon passes the cerclage cable 13 through the aperture 59 of the head 58 for the positioning pin 16. The insertion of the cerclage cable 13 through the aperture 59 in the positioning pin 16 secures the cerclage cable 13 with the bone plate 17 thereby preventing a disengagement of the cerclage cable 13 from the bone plate 12 during an exertion of a tensioning force upon the cerclage cable 13 by the tension plate 12. Upon inserting the cerclage cable 13 through the aperture 59 in the positioning pin 16 connected with the bone plate 17, the surgeon completes deployment of the cerclage system 10 as previously described. After release of the tension plate 12 from the forceps 81 and the subsequent continuous compressing of the bone 90 by the cerclage system 10, the bone plate 17 assists in affixing the bone 90 in order to promote a fusion and a subsequent healing thereof.

Although FIG. 12 illustrates use of a bone plate 17 including the first opening 72, the second opening 73, and the third opening 74, one of ordinary skill in the art will recognize alternative uses and configurations for the bone plate 17. Illustratively, the positioning pin 15 or the positioning pin 16 may be connected with the bone plate 17 using the first opening 72 or the second opening 73 while the third opening 74 is utilized to secure the bone plate 17 with the bone 90 via a bone screw. Moreover, additional openings in the bone plate 17 may be used to secure the bone plate 17 with the bone 90 via bone screws.

In view of the foregoing embodiments illustrating the cerclage system 10 according to the present invention, it should be understood that a cerclage system will fall within the scope of the present invention regardless of the shape of the tension plate or the number of apertures therein provided the tension plate delivers the energy stored therein to a cerclage cable of a cerclage system. Moreover, although the present invention has been described in terms of the foregoing embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. A cerclage system adapted to affix a bone, comprising:
a cerclage cable being adapted to encircle the bone;
a tension plate moveable between a natural shape and an insertion shape whereby the tension plate stores energy;
a positioning pin being adapted to engage the cerclage cable, the positioning pin further being adapted to engage the tension plate thereby securing the positioning pin with the tension plate;
a cable lock being adapted to lock the cerclage cable about the bone in engagement with the tension plate using the positioning pin; and
the tension plate being adapted for positioning atop the bone while residing in the insertion shape, whereby the tension plate, through an engagement thereof with the cerclage cable using the positioning pin and upon attempted movement thereof from the insertion shape toward the natural shape, delivers the energy stored therein to the cerclage cable thereby tensioning the cerclage cable such that the cerclage system continuously compresses the bone.

2. The cerclage system of claim 1, the tension plate, comprising:
a base;
a first arm extending from the base to a distal end;
a second arm extending from the base to a distal end; and
the base proximate the first arm and the second arm including a transition section.

3. The cerclage system of claim 2, wherein:
the tension plate in the natural shape, comprising the base through the transition section thereof moving the first arm and the second arm to locate the first arm and the second arm in a natural position whereby the first arm and the second arm expand such that the first arm at the distal end thereof and the second arm at the distal end thereof are spaced apart at a first distance; and
the tension plate in the insertion shape, comprising the base through the transition section thereof deforming to store energy while moving the first arm and the second arm to locate the first arm and the second arm in an insertion position whereby the first arm and the second arm contract such that the first arm at the distal end thereof and the second arm at the distal end thereof are spaced apart at a second distance that is less than the first distance.

4. The cerclage system of claim 3, the engagement of the tension plate with the cerclage cable, comprising the first arm and the second arm engaging the cerclage cable.

5. The cerclage system of claim 4, wherein, as the tension plate attempts movement from the insertion shape toward the natural shape, the base through the transition section thereof attempts to move the first arm and the second arm from the insertion position to the natural position, whereby the first arm and the second arm attempt to expand, further whereby the first arm and the second arm tension the cerclage cable such that the cerclage system continuously compresses the bone.

6. The cerclage system of claim 4, the first arm including at least a first aperture being adapted to receive a fixation device that secures the tension plate with the bone.

7. The cerclage system of claim 6, wherein, as the tension plate attempts movement from the insertion shape toward the natural shape, the base through the transition section thereof attempts to move the first arm and the second arm from the insertion position to the natural position, whereby the second arm, due to a securing of the first arm with the bone, attempts to expand from the first arm, further whereby the second arm tensions the cerclage cable such that the cerclage system continuously compresses the bone.

8. The cerclage system of claim 3, comprising:
the first arm including at least a first aperture; and
the positioning pin being adapted to engage the cerclage cable, the positioning pin further being adapted to fit within the first aperture of the first arm thereby securing the positioning pin with the tension plate.

9. The cerclage system of claim 8, the engagement of the tension plate with the cerclage cable, comprising the first arm engaging the cerclage cable through a coupling of the cerclage cable with the positioning pin fit within the first aperture of the first arm and the second arm engaging the cerclage cable.

10. The cerclage system of claim 9, wherein, as the tension plate attempts movement from the insertion shape toward the natural shape, the base through the transition section thereof attempts to move the first arm and the second arm from the insertion position to the natural position, whereby the first arm and the second arm attempt to expand, further whereby the first arm and the second arm tension the cerclage cable such that the cerclage system continuously compresses the bone.

11. The cerclage system of claim 3, comprising:
the first arm including at least a first aperture being adapted to receive a fixation device that secures the tension plate with the bone and a second aperture; and
the positioning pin being adapted to engage the cerclage cable, the positioning pin further being adapted to fit within the second aperture of the first arm thereby securing the positioning pin with the tension plate.

12. The cerclage system of claim 11, the engagement of the tension plate with the cerclage cable, comprising the first arm engaging the cerclage cable through a coupling of the cerclage cable with the positioning pin fit within the second aperture of the first arm and the second arm engaging the cerclage cable.

13. The cerclage system of claim 12, wherein, as the tension plate attempts movement from the insertion shape toward the natural shape, the base through the transition section thereof attempts to move the first arm and the second arm from the insertion position to the natural position, whereby the second arm, due to a securing of the first arm with the bone, attempts to expand from the first arm, further whereby the second arm tensions the cerclage cable such that the cerclage system continuously compresses the bone.

14. The cerclage system of claim 3, comprising:
the first arm including a first aperture and a second aperture being adapted to receive a fixation device that secures the tension plate with the bone and a third aperture; and
the positioning pin being adapted to engage the cerclage cable, the positioning pin further being adapted to fit within the third aperture of the first arm thereby securing the positioning pin with the tension plate.

15. The cerclage system of claim 14, the first arm including the first aperture located adjacent the base of the tension plate, the second aperture located adjacent the distal end of the first arm, and the third aperture located between the first aperture and the second aperture.

16. The cerclage system of claim 14, the engagement of the tension plate with the cerclage cable, comprising the first arm engaging the cerclage cable through a coupling of the cerclage cable with the positioning pin fit within the third aperture of the first arm and the second arm engaging the cerclage cable.

17. The cerclage system of claim 16, wherein, as the tension plate attempts movement from the insertion shape toward the natural shape, the base through the transition section thereof attempts to move the first arm and the second arm from the insertion position to the natural position, whereby the second arm, due to a securing of the first arm with the bone, attempts to expand from the first arm, further whereby the second arm tensions the cerclage cable such that the cerclage system continuously compresses the bone.

18. The cerclage system of claim 1, comprising a bone plate being adapted to engage the cerclage cable, the bone plate further being adapted to engage the bone, whereby, upon the tension plate tensioning the cerclage cable, the bone plate assists in continuously compressing the bone.

* * * * *